(12) United States Patent
Oyamada et al.

(10) Patent No.: US 8,999,730 B2
(45) Date of Patent: Apr. 7, 2015

(54) IMMUNOCHROMATOGRAPHY METHOD (75) Inventors: Takayoshi Oyamada, Kanagawa (JP); Junichi Katada, Kanagawa (JP); Kenji Narahara, Tosu (JP); Daisuke Ogata, Tosu (JP); Tomonori Takeshige, Tosu (JP); Akihiko Onodera, Tosu (JP)

(73) Assignee: FUJIFILM Corporation, Tokyo (JP)

( * ) Notice: Subject to any disclaimer, the term of this patent is extended or adjusted under 35 U.S.C. 154(b) by 514 days.

(21) Appl. No.: 12/961,140

(22) Filed: Dec. 6, 2010

(65) Prior Publication Data
US 2011/0136142 A1    Jun. 9, 2011

(30) Foreign Application Priority Data

Dec. 7, 2009 (JP) ................................. 2009-277643

(51) Int. Cl.
G01N 33/58 (2006.01)
G01N 33/543 (2006.01)
G01N 33/558 (2006.01)

(52) U.S. Cl.
CPC ........ G01N 33/54393 (2013.01); G01N 33/585 (2013.01); G01N 33/558 (2013.01)

(58) Field of Classification Search
USPC ....................................................... 436/514
See application file for complete search history.

(56) References Cited

U.S. PATENT DOCUMENTS

| 4,487,830 | A * | 12/1984 | Coates et al. | 435/7.23 |
| 5,876,944 | A * | 3/1999 | Kuo | 435/7.1 |
| 8,043,866 | B2 * | 10/2011 | Oyamada et al. | 436/514 |
| 2007/0141717 | A1 * | 6/2007 | Carpenter et al. | 436/172 |
| 2008/0160549 | A1 * | 7/2008 | Oyamada et al. | 435/7.94 |
| 2008/0166821 | A1 * | 7/2008 | Oyamada et al. | 436/536 |
| 2009/0111196 | A1 | 4/2009 | Oyamada et al. | |
| 2009/0246886 | A1 * | 10/2009 | Buck | 436/501 |

FOREIGN PATENT DOCUMENTS

| EP | 2065706 A2 * | 6/2009 |
| JP | 2002-202307 A | 7/2002 |

(Continued)

OTHER PUBLICATIONS

Extended European Search Report dated Feb. 16, 2011 for Application No. 10193778.7.

Primary Examiner — Melanie Y Brown
Assistant Examiner — Rebecca Martinez
(74) Attorney, Agent, or Firm — Birch, Stewart, Kolasch & Birch, LLP (57) ABSTRACT It is an object of the present invention to provide an immunochromatography method capable of measuring a sample in a low concentration range and a high concentration range by setting the measurable range of the sample much wider than the conventional measurable range. The present invention provides an immunochromatography method, which comprises: spreading a test substance, a first labeling substance modified with a first binding substance that binds to the test substance, and a second labeling substance modified with the first binding substance that binds to the test substance, which are in a mixed state, on an insoluble carrier; and capturing the test substance, the first labeling substance, and/or the second labeling substance at a reaction site on the insoluble carrier having a substance having ability to bind to the first binding substance that binds to the test substance, so as to detect the test substance, wherein the first labeling substance is a labeling substance that causes an amplification reaction, and the second labeling substance is a labeling substance that does not substantially influence on the amplification reaction.

3 Claims, 1 Drawing Sheet

(56) References Cited

FOREIGN PATENT DOCUMENTS

| | | | |
|---|---|---|---|
| JP | 3309977 B2 | 7/2002 |
| JP | 2009-98139 A | 5/2009 |
| WO | WO 93/03176 A1 | 2/1993 |

\* cited by examiner

IMMUNOCHROMATOGRAPHY METHOD

TECHNICAL FIELD

The present invention relates to a measurement method wherein an immunochromatography method is used, and a test kit wherein an immunochromatography method is used.

BACKGROUND ART

Among physiologically active substances or environmental pollutants such as natural products, toxins, hormones or agricultural chemicals, numerous substances act in ultratrace amounts. Accordingly, instrumental analytical methods capable of performing high-sensitivity analysis have conventionally been widely used for qualitative and quantitative measurement of these substances. However, instrumental analytical methods are poor in specificity, require excessive time for analysis including pretreatment of samples, and comprise complicated operations. Thus, instrumental analytical methods are inconvenient for the purpose of rapid and convenient measurements that have been required in recent years. Meanwhile, immunoassays are highly specific and much easier in terms of operation than instrumental analytical methods. Therefore, immunoassays have gradually spread in the field of measurement of physiologically active substances and environmental pollutants. However, conventional immunoassays such as enzyme immunoassays using 96-well plates and latex agglutination assays do not always provide satisfactory rapidness and convenience for measurement or detection sensitivity.

Another need expected to be enabled is as follows. Achievement of higher sensitivity of tests that currently use relatively invasive samples such as swabs and blood makes it possible to detect very small amounts of analytes contained in relatively low-invasive samples such as snot, gargle water, and urine. Thus, it can be anticipated to develop a test method which has less burden on patients.

In recent years, a test kit (hereinafter referred to as an immunochromatography kit), in which an immunochromatography method (hereinafter also referred to as an immunochromatography or an immunochromato method) is used, has been used more often in examination of infections that require particularly rapid diagnosis. According to the spread of these kits, patients with infections can be identified by a rapid and convenient method, and subsequent diagnosis and therapy can be conducted immediately and accurately. For example, in an immunochromatography method using the sandwich method, a labeled second antibody capable of specifically binding to an analytical target (for example, an antigen) and a sample solution which may possibly contain the analytical target are spread on an insoluble thin-membrane support (for example, a glass fiber membrane, a nylon membrane, cellulose membrane, etc.) on which a first antibody capable of specifically binding to the analytical target has been immobilized in a specific region. As a result, an immune complex with the analytical target is formed in the region of the insoluble thin-membrane support on which the first antibody has been immobilized. The analytical target can be measured by detecting a signal such as the color development or coloring of a labeling substance. The labeling substance to be used herein may be, for example, a protein including an enzyme, colored latex particles, metal colloids, or carbon particles.

The immunochromatography method requires neither massive facilities nor instruments for determination and measurement. Furthermore, the immunochromatography method is simple in operation, and thus, measurement results are obtained only by adding dropwise a sample solution which may possibly contain an analytical target and then leaving it at rest for approximately 5 to 15 minutes. Thus, since the immunochromatography method promptly gives measurement results, this technique is widely used as a convenient, rapid, and highly specific method for determination and measurement in many scenarios, such as for clinical examination in hospitals and in assays in laboratories.

With regards physiologically active substances or environmental pollutants such as natural products, toxins, hormone or agricultural chemicals, and further samples in an initial phase of being infected with virus infection, many substances exert their effects in ultratrace amounts that are undetectable by conventional common immunochromatography methods. Therefore, there are demands for development of rapid, convenient, and highly sensitive immunochromatography methods for such substances.

On the other hand, by applying the principle of such an immunochromatography method, using a reader for optically measuring the optical density of a detection site, the presence of a test substance can be qualitatively confirmed, or such a test substance can also be quantified. As with the Cobas h232 series of Roche Diagnostics, there may also be a case in which the blood concentration of a protein known as a myocardial marker is promptly measured for approximately 15 minutes by quantifying it according to the immunochromatography method.

However, conventionally, the measurable range of the conventional immunochromato method using a gold colloid, a colored latex or the like as a labeling substance has been limited with regard to the low concentration range of a test substance due to the limitation of the absorbance per gold colloid particle or colored latex particle. Moreover, in order to solve the aforementioned problem, if the signal of gold colloid is amplified with silver ions, for example, the problem regarding low concentration range can be solved. However, the following problems would often occur (JP Patent Publication (Kokai) No. 2009-098139). That is, even if the amount of silver is increased, shield area is not changed so much, and thus, the absorbance in a high concentration range gets saturated. Further, if a large amount of gold colloid is used in order to ensure a measurable range in a low concentration range, a problem regarding false-positive results would be created by a non-specifically adsorbed gold colloid labeling substance, for example, together with the amplification of the signal. Thus, if the amount of the labeling substance is reduced to a level at which false-positive results are not obtained, there may be a case in which a phenomenon whereby an antigen becomes negative in an ultrahigh concentration range is observed due to what is called a prozone phenomenon.

The achievement of high sensitivity according to an enzyme method or a silver amplification method has been previously known (Japanese Patent No. 3309977; JP Patent Publication (Kokai) No. 2002-202307). However, there have been no systems capable of ensuring a wide sufficient measurable range from a low concentration range to a high concentration range.

SUMMARY OF THE INVENTION

As described above, the immunochromatography method in which a conventional labeling substance is used has been problematic in terms of a narrow measurable range. In addition, in order to enable measurement at a low concentration, it has been difficult to measure a high concentration of sample only by measuring a signal obtained after amplification.

That is to say, it is an object of the present invention to provide an immunochromatography method capable of measuring a sample in a low concentration range and a high concentration range by setting the measurable range of the sample much wider than the conventional measurable range. In an amplification system, it has been necessary to carry out an amplification reaction with the use of a substrate or a reagent. Hence, it has been necessary that a sample is added dropwise and spreading is once carried out due to capillarity, and that, after a certain period of time, such a substrate or reagent is spread again. In general, in order to reduce noise, the sensitivity before amplification must be set at low, the detection sensitivity thereby becomes a level that cannot be determined by visual observation. As a result, regardless of the concentration of a test substance in the sample, nothing could have been done but waiting for a certain period of time. Furthermore, if the amount of a labeling substance or the like has been decreased to reduce noise, it has caused a problem regarding false-negative results in an ultrahigh concentration range due to a prozone phenomenon.

In the present invention, two different types of labeling substances are used, For example, using one type of labeling substance, measurement is carried out by visual observation or using an adequate apparatus or the like. Thereafter, the amplification of the other type of labeling substance is carried out, and measurement is carried out again. Thus, by carrying out measurement twice before and after amplification, it became possible to carry out measurement in a low concentration range and a high concentration range, and as a result, the measurable range of the sample could be widened in comparison with the conventional measurable range.

Thereby, in the diagnosis of infection disease and the like, in the case of a sample in a high concentration range, it becomes possible to confirm signal in a short time by visual observation or the like even before amplification. As a result, positive determination can be made at an early stage before the amplification treatment, and the measurement can be terminated, as necessary. On the other hand, results can be given even in a low concentration range in which the test substance is present in an extremely small amount or in an ultrahigh concentration range in which a prozone phenomenon may occur, without problems regarding false-negative results. Moreover, in diagnostic items that require quantitative measurement, it has become possible to carry out measurement in an extremely wide range.

The present invention provides an immunochromatography method, which comprises: spreading a test substance, a first labeling substance modified with a first binding substance that binds to the test substance, and a second labeling substance modified with the first binding substance that binds to the test substance, which are in a mixed state, on an insoluble carrier; and capturing the test substance, the first labeling substance, and/or the second labeling substance at a reaction site on the insoluble carrier having a substance having ability to bind to the first binding substance that binds to the test substance, so as to detect the test substance, wherein the first labeling substance is a labeling substance that causes an amplification reaction, and the second labeling substance is a labeling substance that does not substantially influence on the amplification reaction.

Preferably, the first labeling substance is a substance that reacts with silver ions and a reducing agent used for such silver ions to generate metallic silver, and the second labeling substance is a substance that does not substantially have a reactivity with silver ions and a reducing agent used for the silver ions.

Preferably, the metallic silver is generated as a result of an amplification reaction using silver ions and a reducing agent used for the silver ions.

Preferably, the first labeling substance is a metal colloid.

Preferably, the number of metal colloid particles contained in the insoluble carrier is from $1\times10^5$ or more to $1\times10^8$ or less.

Preferably, the metal colloid includes gold, silver or platinum.

Preferably, the first labeling substance is an enzyme and the amplification reaction is an enzyme reaction.

Preferably, the second labeling substance is a colored particle.

Preferably, the second labeling substance is a colored latex.

Preferably, the mean particle size of the first labeling substance at the time of measurement is from 1 μm or more to 20 μm or less.

According to the chromatography method of the present invention, the measurable range of a sample can be widened by approximately two digits from the conventional range, and as a result, it becomes possible to carry out measurement from a low concentration range to a high concentration range. Furthermore, in the prozone phenomenon of an ultrahigh concentration range occurring in the system of a labeling substance for amplification, in which the amount of the labeling substance has been reduced, a test substance can also be detected by adding a second labeling substance without generation of false-negative results.

Still further, a determination time is fixed when an amplification system is used. In contrast, in the case of a high concentration of sample in a range in which determination can be carried out by visual observation, determination can be carried out using a labeling substance that does not need amplification, and thus, determination can be carried out in a short time.

BRIEF DESCRIPTION OF THE DRAWINGS

FIG. 1 is a longitudinal sectional view schematically showing the longitudinal section of an immunochromatography kit that can be used in the present invention. 1: back adhesive sheet; 2: labeled antibody-holding pad; 3: antibody-immobilized membrane; 3a: capturing site; 31: detection portion; 32: control portion; 4: absorbent pad (liquid-absorbing portion); 5: sample-adding pad (dropping portion).

MODE FOR CARRYING OUT THE INVENTION

As the mode for carrying out the present invention, the present invention can be carried out using an immunochromatography method, which comprises: spreading a test substance and a labeling substance modified with a first binding substance that binds to the test substance, which are in a mixed state, on an insoluble carrier; and capturing the test substance and the labeling substance at a reaction site on the insoluble carrier having a second binding substance that binds to the test substance or a substance having ability to bind to the first binding substance that binds to the test substance, so as to detect the test substance, wherein the method has at least two types of labeling substances, namely, a first labeling substance that causes an amplification reaction and a second labeling substance that does not substantially influence on such an amplification reaction.

In carrying out the present invention, it is preferable to use at least two different types of labeling substances, namely, (a) a first labeling substance having the property of reacting with silver ions and a reducing agents used for such silver ions to generate metallic silver, and (b) a second labeling substance having the property of having no reactivity or only an extremely low level of reactivity with silver ions and a reducing agent used for such silver ions.

As a labeling substance used in the present invention, which generates metallic silver as a result of the reaction with silver ions and a reducing agent used for such silver ions, a metal colloid including gold, silver or platinum can be used. In addition, in carrying out the present invention, the particle number of the metal colloid contained as a first labeling substance in one test strip is preferably set between $1 \times 10^5$ or more and $1 \times 10^8$ or less.

As a second labeling substance that does not have reactivity with silver ions and a reducing agent used for such silver ions, a colored particle other than the metal colloid can be used. The type of such colored particle is not particularly limited. A colored latex is preferable.

In the amplification reaction of the present invention, the size of a labeling substance before initiation of the test may be different from the size thereof at the termination of the test. For example, when a metal colloid is used as a first labeling substance and metallic silver is then generated by the reaction of the first labeling substance with silver ions and a reducing agent used for such silver ions, the size of such a colloid particle before amplification is generally between approximately 0.01 μm or more and 0.10 μm or less. In contrast, the mean particle size of such a labeling substance after amplification at the termination of the test is preferably between 1 μm or more and 20 μm or less.

1. Immunochromatography

In general, immunochromatography method is a means for determining and/or measuring an analytical sample simply, promptly and specifically by the following procedures. That is to say, a chromatographic carrier having at least one reaction site comprising an immobilizing reagent (an antibody, an antigen, etc.) capable of binding to an analytical sample is used as a stationary phase. On this chromatographic carrier, a dispersion liquid prepared by dispersing a labeling substance modified with a reagent capable of binding to an analytical target is used as a mobile phase, and it is allowed to move in the chromatographic carrier in a chromatographic manner. At the same time, while the analytical target specifically binds to the labeling substance, they reach the reaction site. The chromatography method is a means for qualitatively and quantitatively analyzing the presence of a detection product in a solution to be analyzed, by visual observation or using an adequate apparatus, utilizing the fact that a labeling substance is concentrated in the immobilizing reagent portion, only in a case in which an analytical target is present in the solution to be analyzed as a result of the specific binding of a complex consisting of the analytical target and the labeling substance to the immobilizing reagent in the reaction site.

The kit or apparatus for carrying out the chromatography method of the present invention may comprise a silver-containing compound and a reducing agent used for silver ions. The complex consisting of the analytical target and the labeling substance, which has bound to the immobilizing reagent, is used as a nucleus, and signal is amplified by an amplification reaction. As a result, high sensitivity can be achieved. According to the present invention, high-sensitivity chromatography can be promptly carried out 2. Test Sample A test sample that can be analyzed by the chromatography method of the present invention is not particularly limited, as long as it is a sample that may possibly contain an analytical target. Examples of such a sample include: biological samples; and in particular, animals' (particularly, humans') body fluids (for example, blood, serum, plasma, spinal fluid, lacrimal fluid, sweat, urine, pus, snot or sputum), excreta (for example, feces), organs, tissues, mucosa and skins; swab samples and gargle water that may possibly contain the aforementioned samples; animals and plants themselves; and the dried products thereof.

3. Pretreatment of Test Sample

In the chromatography method of the present invention, the aforementioned test sample may be directly used, or the test sample may be used in the form of an extract obtained by extracting it with a suitable extraction solvent Otherwise, the test sample may also be used in the form of a diluted solution obtained by diluting the above-mentioned extract with a suitable diluent, or in the form of a condensate obtained by concentrating the above-mentioned extract by a suitable method. As the above-mentioned extraction solvent, a solvent used in ordinary immunological analysis (for example, water, a normal saline, a buffer, etc.) or a water-miscible organic solvent that can directly carry out an antigen-antibody reaction by being diluted with the above-mentioned solvent, can also be used.

4. Constitution

The type of a chromatographic strip that can be used in the chromatography method of the present invention is not particularly limited, as long as it can be used in ordinary chromatography methods. For example, FIG. 1 schematically shows a sectional view of an example of the chromatographic strip of the present invention.

Figure 1:
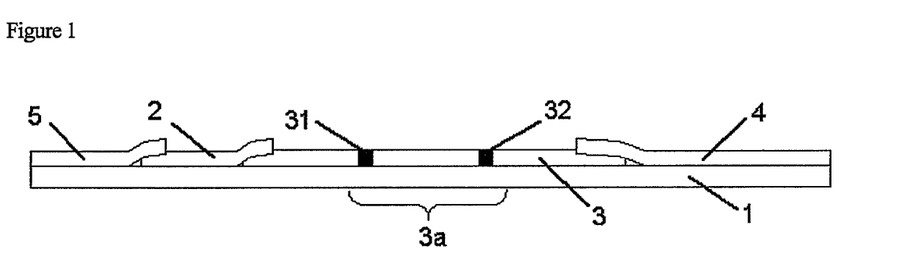

FIG. 1 will be described. In the chromatographic strip of the present invention, a sample-adding pad 5, a labeling substance-holding pad 2 (for example, a gold colloid antibody-holding pad), a chromatographic carrier 3 (for example, an antibody-immobilized membrane), and an absorbent pad 4 are disposed in this order on an adhesive sheet 1, from the upstream of a spreading direction towards the downstream thereof.

The chromatographic carrier 3 has a capturing site 3*a*, and also has a detection zone 31 (which is also referred to as a detection portion) that is a region on which an antibody or an antigen specifically binding to an analytical target has been immobilized. As desired, it may also have a control zone 32 (which is also referred to as a control portion) that is a region on which a control antibody or antigen has been immobilized.

The labeling substance-holding pad 2 can be produced by preparing a suspension containing a labeling substance, applying the suspension to a suitable absorbent pad (for example, a glass fiber pad), and then drying it As the above-described sample-adding pad 5, a glass fiber pad can be used, for example.

4-1. Labeling Substances

The present invention is characterized in that at least two types of labeling substances are used. A first labeling substance is a labeling substance that is able to cause an amplification reaction. The first labeling substance can be used in enzyme labeling to continuously form pigments with an enzyme and the substrate thereof (a pigment amplification solution), or can be used in metal colloid particle labeling to form silver particles as a result of a reduction reaction in the presence of silver ions.

On the other hand, a second labeling substance is a substance that does not substantially influence on an amplification reaction. As such a second labeling substance, a colored particle used in immune agglutination or immunostaining can be used, for example. Specifically, a colored latex particle that is a fine particle of high molecular weight polymer, a liposome or a microcapsule containing pigments and the like can be used. It is desirable that these substances directly have strong signals in a visible region and do not substantially have a significant influence on the above-described amplification reaction. All these substances are bound to ingredients that cause an immune reaction specific to a test substance in the immunochromato method, and especially, to antibodies, and they are then used.

A particularly preferred labeling substance is a colored latex particle made of polystyrene, which has a particle size of approximately 0.2 to 0.5 μm. In addition, when an enzyme labeling substance is used as a first labeling substance, a metal colloid particle labeling substance may be used as a second labeling substance.

According to the present invention, a metallic labeling substance can be amplified in the immunochromatography method, in which a metal colloid labeling or metallic sulfide labeling substance, other metallic alloy labeling substances (hereinafter referred to as a "metallic labeling substance" at times), or polymer particle labeling substances containing metal are used Specifically, after the aforementioned complex consisting of the analytical target and the labeling substance has been formed, silver ions supplied from a compound containing silver, such as inorganic silver salts or organic silver salts, and a reducing agent used for such silver ions, are allowed to come into contact with the complex, so that the silver ions can be reduced by the reducing agent to generate silver particles. Thereafter, the silver particles are deposited on the above-described metallic labeling substance serving as a nucleus. Thus, the metallic labeling substance can be amplified, and the analysis of the analytical target can be carried out with high sensitivity.

Accordingly, in the immunochromatography method of the present invention, the conventionally known immunochromatography method can be directly applied, with the exceptions that a reaction of depositing, on an immune complex of a labeling substance, silver particles generated as a result of the reduction action of silver ions caused by a reducing agent, is carried out, and that the thus amplified labeling substance is then analyzed.

In the chromatography method of the present invention, as a labeling substance used to label an antibody or an antigen specifically binding to an analytical target (an antigen or an antibody), or a standard compound, a metal colloid labeling substance or a metal sulfide labeling substance is used.

The type of the above-mentioned metal colloid labeling substance or metallic sulfide labeling substance is not particularly limited, as long as it is a labeling substance that can be used in ordinary chromatography methods. Examples of such a metal colloid labeling substance include a platinum colloid, a gold colloid, a palladium colloid, a silver colloid, and a mixture thereof. Examples of such a metallic sulfide labeling substance include the sulfides of iron, silver, palladium, zinc, copper, cadmium, bismuth, antimony, tin and mercury. In the immunochromatography method of the present invention, one or more from these metal colloid labeling substances and/or metallic sulfide labeling substances can be used as a labeling substance(s).

4-2. Binding Substance

In the present invention, the labeling substance is modified with a first binding substance that binds to a test substance. Any compound may be used as such a first binding substance, as long as it has an affinity for the test substance. Examples of the first binding substance include an antibody that reacts with a test substance (an antigen), an antigen that reacts with a test substance (an antibody), and an aptamer that reacts with a test substance (a protein, a low molecular weight compound, etc.).

In the present invention, the porous carrier has (a) a second binding substance that binds to a test substance, or (b) a substance having ability to bind to the first binding substance. Any compound may be used as such a second binding substance that binds to the test substance, as long as it has an affinity for the test substance. Examples of the second binding substance include an antibody that reacts with a test substance (an antigen), an antigen that reacts with a test substance (an antibody), and an aptamer that reacts with a test substance (a protein, a low molecular weight compound, etc.). The second binding substance may be either different from or identical to the first binding substance. The substance having ability to bind to the first binding substance that binds to a test substance may be either the test substance itself; or a compound having a site recognized by the first binding substance. An example of such a compound is a compound formed by binding a derivative of a test substance to a protein (for example, BSA).

Preferably, the first binding substance is an antibody, and/or the second binding substance is an antibody. In the immtmochromatography method of the present invention, the type of an antibody having specificity to an analytical target is not particularly limited. Examples of an antibody having specificity to an analytical target that can be used herein include: an antiserum prepared from the serum of an animal immunized with the analytical target; an immunoglobulin fraction purified from the antiserum; a monoclonal antibody obtained by cell fusion using the splenic cells of an animal immunized with the analytical target; and an fragment thereof [for example, F(ab')2, Fab, Fab' or Fv]. These antibodies can be prepared according to ordinary methods.

4-3. Chromatographic Carrier

As a chromatographic carrier, a porous carrier is preferable. A nitrocellulose membrane, a cellulose membrane, an acetylcellulose membrane, a polysulfone membrane, a polyethersulfone membrane, a nylon membrane, a glass fiber, a nonwoven cloth, a cloth, a thread, and the like are particularly preferable.

In general, a detection zone is prepared by immobilizing a detection substance on a part of a chromatographic carrier. Such a detection substance may be directly immobilized on a part of a chromatographic carrier via a physical or chemical bond, or the detection substance may also be allowed to physically or chemically bind to a fine particle such as a latex particle, and the particle may be then trapped in a part of a chromatographic carrier. After immobilization of a detection substance on such a chromatographic carrier, the chromatographic carrier may be preferably subjected to a non-specific adsorption prevention treatment, such as a treatment with an inactive protein, before use.

4-4. Sample-Adding Pad

As materials used for a sample-adding pad, materials having characteristics regarding uniformity, such as a cellulose filter, a glass fiber, polyurethane, polyacetate, cellulose acetate, nylon and a cotton cloth may be used. However, examples of the material for a sample-adding pad are not limited thereto. A sample-adding portion does not only receive a sample containing an analytical target added, but also has a function to filtrate insoluble particles and the like contained in the sample. In addition, in order to prevent an analytical target contained in the sample from non-specifically adsorbing on the material of the sample-adding portion and thereby decreasing analytical precision during analysis, the material that constitutes the sample-adding portion may be previously subjected to a non-specific adsorption prevention treatment before use.

4-5. Labeling Substance-Holding Pad

Examples of a material used for a labeling substance-holding pad include a cellulose filter, a glass fiber, and a nonwoven cloth. Such a material is prepared by being impregnated with a predetermined amount of the labeling substance as prepared above and then being dried.

4-6. Absorbent Pad

An absorbent pad is a site, which physically absorbs the added sample via chromatographic transport and which also absorbs and eliminates an unreacted labeling substance and the like that are not insolubilized in the detection portion of a chromatographic carrier. As such an absorbent pad, water-absorbing materials such as a cellulose filter, a nonwoven cloth, a cloth and cellulose acetate can be used. The chromatographic speed after the chromatography tip of the added sample has arrived at the absorbing portion is different depending on the material of an absorbing material, the size thereof, etc. Thus, by selecting such conditions, the chromatographic speed suitable for the measurement of an analytical target may be determined.

5. Immunological Test Method

Hereinafter, a sandwich method, which is a specific embodiment of the chromatography method of the present invention, will be described.

In the sandwich method, procedures are not particularly limited. For example, the following procedures may be used for the analysis of a test substance. First, a first antibody and a second antibody having specificity to a test substance (an antigen) have previously been prepared by the above-described methods. In addition, the first antibody has previously been labeled. The second antibody is immobilized on a suitable first insoluble carrier (for example, a nitrocellulose membrane, a glass fiber membrane, a nylon membrane or a cellulose membrane), and it is then allowed to come into contact with a test sample (or an extract thereof) that may possibly contain the test substance (antigen). As a result, if the test substance is actually present in the test sample, an antigen-antibody reaction occurs. This antigen-antibody reaction can be carried out in the same manner as an ordinary antigen-antibody reaction. At the same time of the antigen-antibody reaction, or after completion of the antigen-antibody reaction, an excessive amount of the labeled first antibody is further allowed to come into contact with the test sample. As a result, if the test substance is present in the test sample, an immune complex consisting of the immobilized second antibody, the test substance (antigen) and the labeled first antibody is formed.

In the sandwich method, after the reaction of the immobilized second antibody, the test substance (antigen) and the first antibody has been completed, the labeled first antibody, which has not formed the above-described immune complex, is eliminated, and a first optical density measurement is then performed on a region on a first insoluble carrier, in which the immobilized second antibody has been immobilized, so as to quantify the labeling substance, thereby measuring the amount of the test substance in the test sample. Subsequently, a signal from the labeling of the labeled first antibody that has formed the above-described immune complex is amplified by supplying metal ions and a reducing agent, and a second optical density measurement is then carried out. Thereby, the labeling substance after completion of the amplification can be quantified, and thus, the amount of the test substance in the test sample can be measured.

6. Washing

The present invention comprises: a step of measuring the captured at least one type of labeling substance; and a step of measuring a labeling substance different from the aforementioned labeling substance. Between the two steps, amplification of the labeling substance may be carried out. In such a case, washing may be carried out using a washing solution between those steps.

(Washing Solution)

Any washing solution may be used to eliminate the labeled first antibody, which has not formed the above-described immune complex, as long as it has a washing function.

The type of such a washing solution is not particularly limited, as long as it is a liquid for washing the labeling substance that remains in the chromatographic carrier except for the labeling substance remaining as a result of a specific binding reaction, namely, a non-specifically remaining labeling substance. Simple water, or a single solvent such as ethanol, may be used as such a washing solution. Further, for example, a 1% BSA-containing PBS buffer, a surfactant solution, or the like may be used. Moreover, as such a washing solution, a liquid containing silver ions or a liquid containing a reducing agent used for such silver ions, as described later, may also be used. The washing solution is spread while it washes a non-specifically remaining labeling substance during the spreading. As a result, it is spread while it contains the labeling substance. In order to enhance the washing effects, a liquid that does not contain a labeling substance may be prepared as a washing solution before the spreading. Moreover, in order to increase the washing effects, there may also be used a washing solution, the pH of which has been adjusted, or to which a surfactant ingredient, a protein such as BSA, or a high molecular weight compound such as polyethylene glycol has been added.

(Spreading of Washing Solution and Direction Thereof)

After a sample solution has been spread, a washing solution is added to a chromatographic strip and is used to wash a labeling substance remaining on the chromatographic strip, other than those bound to the sample via an antigen-antibody reaction. Methods for supplying such a washing solution include: a method of directly adding a washing solution to a sample-dropping portion after a sample solution has been spread; a method comprising previously adhering a washing solution-adding pad used for supplying a washing solution to a strip and a water absorbent pad, and then adding the washing solution to the washing solution-adding pad, so as to supply the washing solution to the water absorbent pad direction; a method comprising previously providing a washing solution-adding portion on a strip, and then adding a washing solution to the washing solution-adding portion after a sample solution has been spread; and other methods. A method comprising spreading a sample solution on a strip, adhering a washing solution-adding pad used for supplying the washing solution and a water absorbent pad to the strip, then supplying a washing solution to the washing solution-adding pad, and then spreading the washing solution is more preferable. As a method of supplying a washing solution to a washing solution-adding pad, the washing solution-adding pad may be inserted into a pot that contains a washing solution, or a washing solution may be added dropwise to the washing solution-adding pad.

In the present specification, the term "the spreading direction of a solution containing the analytical target" is used to mean a direction that connects the sample-adding pad with the absorbent pad. The term "the spreading direction of a washing solution" is used to mean a direction that connects the washing solution-adding pad used for supplying a washing solution and the water absorbent pad.

When an angle of 45 to 170 degrees can be made between the spreading direction of an analytical target and the spreading direction of a washing solution, a high washing effect can be obtained. Further, the angle between the spreading direction of the analytical target solution and the spreading direction of the washing solution is preferably 60 to 170 degrees, and more preferably 60 to 150 degrees.

The type of a washing solution-adding pad (which is also referred to as a "second insoluble carrier") is not particularly limited, as long as a washing solution can be added to the pad. Examples of such a washing solution-adding pad that can be used herein include a glass fiber pad, a cellulose membrane, and a nitrocellulose membrane.

The type of a water absorbent pad is not particularly limited, as long as it is a substance capable of absorbing water. Examples of such a washing absorbent pad that can be used herein include cellulose, nitrocellulose, a glass fiber, and a mixture thereof.

7. Amplification Solution

The amplification solution is a solution, which generates colored compounds or emits light as a result of the catalytic reaction of an agent contained therein caused by the action of a labeling substance or a test substance, and which thereby causes the amplification of signals. Examples of such an amplification solution include: a silver ion solution, which causes the precipitation of metallic silver on a metallic labeling substance as a result of physical development and a solution of a phenylenediamine compound and a naphthol compound, which generates pigments by the action of peroxidase as a labeling substance and hydrogen peroxide.

More specifically, there can be used, what are called, developing solutions described in publications commonly used in the field of photographic chemistry (for example, "Kaitei Shashin Kogaku no Kiso—Ginen Shashin Hen—(Revised Edition, Basis of Photographic Chemistry, Silver Halide Photography)," edited by the Society of Photographic Science and Technology of Japan, Corona Publishing Co., Ltd.; "Shashin no Kogaku (Photographic Chemistry)," Akira Sasai, Shashin Kogyo K. K.; "Saishin Shoho Handbook (Latest Prescription Handbook)," Shinichi Kikuchi et al, Amico Shuppan). The type of such a developing solution is not particularly limited, as long as it is what is called a physical developing solution, provided that the developing solution contains silver ion in the liquid and the silver ion is reduced where a metal colloid or the like is used as a core of development Such a developing solution may be used as an amplification solution.

A specific example of the amplification solution that can be used herein is an amplification solution comprising a compound containing silver and a reducing agent used for silver ions. Hereafter, a compound containing silver, a reducing agent used for silver ions, and the like will be described.

(Compound that Contains Silver (Ions))

As a silver ion-containing compound, an organic silver salt, an inorganic silver salt, or a silver complex can be used. A silver ion-containing compound having high solubility in a solvent such as water is preferable. Examples of such a silver ion-containing compound include silver nitrate, silver acetate, silver lactate, silver butyrate, and silver thiosulfate. Of these, silver nitrate is particularly preferable. As a silver complex, a silver complex coordinated with a ligand having a water-soluble group such as a hydroxyl group or a sulfone group is preferable. An example of such a silver complex is hydroxy thioether silver.

The inorganic silver salt or the silver complex preferably comprises silver in an amount of generally 0.001 mole/m$^2$ to 0.2 moles/m$^2$, and preferably 0.01 mole/m$^2$ to 0.05 moles/m$^2$.

(Reducing Agent Used for Silver Ions)

As a reducing agent used for silver ions, any materials, such as inorganic and organic materials, or the mixtures thereof, can be used, as long as they can reduce silver ions to silver.

Preferred examples of an inorganic reducing agent include reducing metal salts and reducing metal complex salts, the valence of each of which are changed with metal ions such as $Fe^{2+}$, $V^{2+}$, or $Ti^{3+}$. When such an inorganic reducing agent is used, it is necessary that the oxidized ion would be subjected to complexation or may be reduced, so as to eliminate or detoxify it. For example, in a system in which $Fe^{2+}$ is used as a reducing agent, a complex of $Fe^{3+}$ as an oxide is formed with citric acid or EDTA, so that the oxidized ions can be detoxified. In the present system, it is preferable to use such an inorganic reducing agent. The metal salt of $Fe^{2+}$ is more preferable.

Moreover, it is also possible to use: main developing agents used as photosensitive materials in wet-type silver halide photography (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or a derivative thereof), and leucodyes); and other materials well known to persons skilled in the present field, such as the material described in U.S. Pat. No. 6,020,117.

As such a reducing agent, an ascorbic acid reducing agent is also preferable. Useful ascorbic acid reducing agents include ascorbic acid, an analogue thereof, an isomer thereof, and a derivative thereof. Preferred examples of such an ascorbic acid reducing agent include D- or L-ascorbic acid and a sugar derivative thereof (for example, γ-lactoascorbic acid, glucoascorbic acid, fucoascorbic acid, glucoheptoascorbic acid and maltoascorbic acid), the sodium salts of ascorbic acid, the potassium salts of ascorbic acid, isoascorbic acid (or L-erythroascorbic acid) or a salt hereof (for example, alkali metal salts, ammonium salts, or salts known in the present technical field), enediol-type ascorbic acid, enaminol-type ascorbic acid, and thioenol-type ascorbic acid. Of these, D-, L-, or D, L-ascorbic acid (and an alkali metal salt thereof) or isoascorbic acid (or an alkali metal salt thereof) are particularly preferable. Of these salts, the sodium salts are preferable. A mixture of these reducing agents may be used, as necessary 8. Pigment Amplification Solution As a pigment amplification solution, there can be preferably used a chromogenic substrate, which is used in horseradish peroxidase detection, as described in "Rinsho Kensa (Clinical Examination), Vol. 41, No. 9, 1020, "$H_2O_2$-POD Kei wo Riyoshita Senshoku (Staining utilizing $H_2O_2$-POD system)."

9. Detection Solution

The "detection solution" is used herein to mean a solution, in which an agent contained therein reacts with a labeling substance, a test substance or the like, and as a result, a change such as discoloration, the generation of a colored compound or light emission occurs therein. Examples of such a detection solution include: a solution of o-cresolphthalein complexion, which gets colored by complexation with a calcium ion as a test substance; and a copper ion solution, which reacts with a protein as a test substance and thereby changes color. In addition, the detection solution also includes a solution of a labeled complex, which specifically binds to a test substance. Examples of such a solution include: labeled DNA or labeled RNA, which detects DNA or RNA by hybridization; and an antibody-sensitized particle or an antibody-labeled enzyme, which detects an antigen.

10. Other Auxiliary Agents

The amplification solution may comprise, as other auxiliary agents, a buffer, an antiseptic, for example, an antioxidant or organic stabilizer, or a speed regulating agent Examples of a buffer that can be used herein include: buffers, in which acetic acid, citric acid, sodium hydroxide or a salt thereof, or tris(hydroxymethyl)aminomethane is used; and other buffers that are commonly used in chemical experiments. Using these buffers as appropriate, the amplification solution can be adjusted to have an optimal pH value. In addition, as an anti-fogging agent, alkylamine can be used as an additive. Dodecylamine is particularly preferable. Moreover, in order to improve the solubility of these additives, a surfactant can be used. $C_9H_{19}$—$C_6H_4$—O—$(CH_2CH_2O)_{50}$H is particularly preferable.

11. Method for Calculating Mean Particle Size in Detection

In detection (after amplification), a test line portion is cut out, and the back side of the sample is then attached to a sample stage using carbon paste. The sample is cut into sections, followed by carbon evaporation. Thereafter, the shape and size of the section are observed under a scanning electron microscope. For example, employing FE-STEM S-5500 manufactured by Hitachi High-Technologies Corporation, the sample surface is observed utilizing reflection electron under SEM at an acceleration voltage of 10 KV. Thereafter, 100 signal particles are selected, and a diameter of a circle corresponding to the projected area of each particle is measured, and the mean value is then calculated. The obtained value is defined as a mean particle size in detection.

Hereinafter, the present invention will be more specifically described in the following examples. However, these examples are not intended to limit the scope of the present invention.

EXAMPLES

Example 1

Detection of Influenza Antigen (Preparation of Labeling Ingredients)

An anti-influenza type A monoclonal antibody (clone number: A60010044P; manufactured by Bios Pacific) was allowed to bind to 0.3-μm colored latex (DC02B; manufactured by Bangs Laboratories) and a 0.06-μm gold colloid (GC60; manufactured by British BioCell International) used as labeling ingredients. The binding operation was carried out according to ordinary methods.

(Preparation of Labeled Antibody-Holding Pad 2)

A solution that contained the anti-influenza type A monoclonal antibody-binding colored latex and the anti-influenza type A monoclonal antibody-binding gold colloid in any given OD concentrations was applied to a glass fiber pad, and it was then dried, so as to prepare an anti-influenza type A monoclonal antibody labeling ingredient-coated pad (a labeled antibody-holding pad 2).

(Preparation of Detection Portion 31)

An anti-influenza type A monoclonal antibody (clone number: M2110169; manufactured by Fitzgerald) was applied in a line shape to a predetermined position of a nitrocellulose membrane (SCHF (registered trademark); Millipore) that was an antibody-immobilized membrane 3 as a porous carrier in an amount of 0.5 μl per test, so as to form a detection portion 31. Moreover, an anti-mouse antibody was also applied to the side downstream of the detection portion 31 in an amount of 0.5 μl per test, so as to form a control portion 32 used for confirmation of the reaction. After completion of the aforementioned application, the antibody was naturally dried and was solidified, so as to prepare an anti-influenza type A monoclonal antibody-solid-phased membrane (an antibody-immobilized membrane 3, on which the detection portion 31 was disposed).

(Preparation of Detection Device)

A filter used as a reagent-adding pad 5 (a dropping portion), an anti-influenza type A monoclonal antibody labeling ingredient-coated pad 2, an anti-influenza type A monoclonal antibody-solid-phased membrane 3, and a filter used as an absorbent pad 4 (a liquid absorbing portion), were each attached onto an adhesive-added resin (a back adhesive sheet 1), such that the edges of these components were each overlapped by approximately 3 mm, thereby producing an influenza type A detecting device.

(Reactivity Test)

(Determination Before Amplification)

An influenza virus type A antigen was dissolved in a Tris buffer that contained 5% Tween20, so as to prepare influenza virus type A solutions having different concentrations used for the test 140 μl of the thus prepared solution was added dropwise to the dropping portion 5. Thereafter, line coloration from labeling ingredients (a gold colloid particle-derived color, a colored latex particle-derived color, or a mixed color thereof), which would appear in the detection portion 31 until 10 minutes after the addition of the antigen solution, was observed by visual observation. Determination was made such that strong coloration was indicated as "++," moderate coloration was indicated as "+" weak coloration was indicated as "+w," and no coloration was indicated as "−." When such line coloration was observed after the addition of the antigen solution, the time at which the coloration strength became "+w" was defined to be a detectable time, and such a detectable time was measured.

(Determination after Amplification)

(Preparation of Silver Amplification Solution)

(Preparation of Amplification Solution A-1)

40 mL of a 1 mold, iron nitrate aqueous solution produced by dissolving iron (III) nitrate nonahydrate (Wako Pure Chemical Industries, Ltd.; 095-00995) in water, 10.5 g of citric acid (Wako Pure Chemical Industries, Ltd.; 038-06925), 0.1 g of dodecylamine (Wako Pure Chemical Industries, Ltd.; 123-00246), and 0.44 g of a surfactant, $C_9H_{19}$—$C_6H_4$—O—$(CH_2CH_2O)_{50}$H were dissolved in 325 g of water. After all the aforementioned components had been dissolved in the water, 40 mL of nitric acid (10% by weight) was added to the mixed solution, while stirring with a stirrer. Thereafter, 80 mL of the solution was weighed, and 11.76 g of iron (II) ammonium sulfate hexahydrate (Wako Pure Chemical Industries, Ltd.; 091-00855) was added thereto. The obtained mixture was defined as amplification solution A-1.

(Preparation of Amplification Solution A-2)

Water was added to 10 mL of a silver nitrate solution (containing 10 g of silver nitrate), resulting in a total amount of 100 g. This solution was defined as amplification solution A-2 (10% by weight of silver nitrate aqueous solution).

(Preparation of Amplification Solution A)

40 mL of amplification solution A-1 was weighed, and 4.25 mL of amplification solution A-2 was then added thereto, followed by stirring. The obtained mixture was defined as amplification solution A.

(Preparation of Washing Solution)

A 1% BSA-containing PBS buffer obtained by dissolving 1% by weight of BSA (Sigma) in a PBS buffer (Wako Pure Chemical Industries, Ltd.) was used as a washing solution.

(Evaluation)

(Washing)

Figure 2:
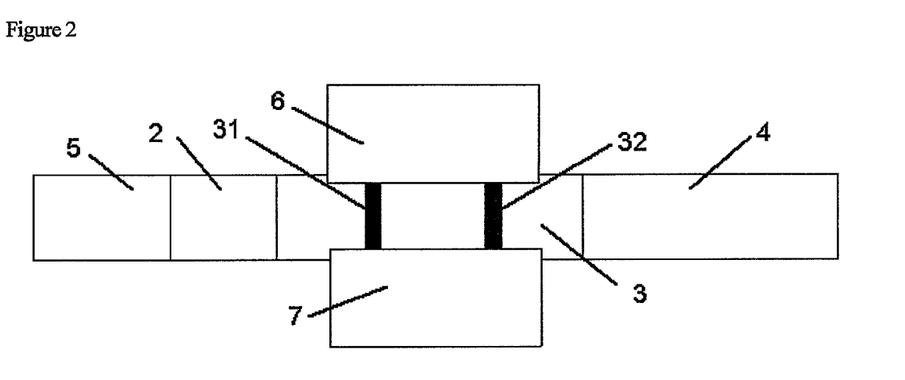
FIG. 2 is an overhead, plain view schematically showing the chromatography kit that can be used in the present invention, to which a washing pad is attached. 2: labeled antibody-holding pad; 3: antibody-immobilized membrane; 31: detection portion; 32: control portion; 4: absorbent pad; 5: sample-adding pad; 6: washing solution-adding pad; 7: washing solution-absorbing pad.

Ten minutes after the addition of the antigen solution, a washing solution-adding pad 6 (a glass fiber filter cut into a size of 12 mm×10 mm (GF/F manufactured by GE Healthcare)) was pressed against the edge (acting as an upstream edge in the spreading of a washing solution) of the membrane of the immunochromatography kit used for the test, which was determined in the detection portion 31, and a washing solution-absorbing pad 7 (a glass fiber filter cut into a size of 12 mm×15 mm (GF/F manufactured by GE Healthcare)) was pressed against the other edge thereof (acting as a downstream edge), so that the 12-mm edge sides became the washing solution upstream side and downstream side, respectively, on the membrane, and so that each pad was overlapped with the membrane by approximately 2 mm. The angle between the washing solution spreading direction and the test substance spreading direction was set at 90 degrees. 150 μL of the washing solution was spread by capillarity, so that the membrane was washed for 3 minutes.

In the present experiment, the height of a liquid level spreading on the shape of a washing solution container during the washing operation, the shape and material of the sample-adding pad of the immunochromatography kit, experimental environment (temperature and humidity), the material and thickness of the absorbent pad, the connection of the absorbent pad with the nitrocellulose membrane, and the like are factors that change the water-absorbing speed and amount of the washing solution. Thus, it is necessary to keep these factors constant in the experiment. The water-absorbing speed and amount of the washing solution absorbed are factors that determine the final washing effects (a decrease in the remaining amount of gold fine particles). This experiment was carried out at an air temperature of 22±3 C.° and a humidity of 50±15%.

(Signal Amplification with Amplification Solution)

After completion of the washing, 100 μL of an amplification solution was added to the membrane, such that the detection zone and control zone thereof were filled with the amplification solution. Thereafter, an amplification reaction was carried out for 1 minute.

After completion of the amplification reaction, the membrane was removed, and it was then fully washed with water for 1 minute. Then, the coloration level of the detection portion 31 was determined by visual observation. Determination was made such that strong coloration was indicated as "++," moderate coloration was indicated as "+," weak coloration was indicated as "+w," and no coloration was indicated as "−."

Example 1

Comparative Examples 1-4

Kits, in which the amounts of colored latex and gold colloid were varied, were produced by the above-described production method, and were then evaluated (Table 1). In Example 1, a kit was produced using an anti-influenza type A monoclonal antibody labeling ingredient in an amount relative to OD=0.050 (corresponding to 1/30 amount of an ordinary concentration for a visual observation kit, and also corresponding to $4 \times 10^7$ gold colloid per kit) at the absorbance of a wavelength of 520 nm and an anti-influenza type A monoclonal antibody-binding colored latex in an amount relative to OD=0.4 at the absorbance of a wavelength of 850 nm. In contrast, in Comparative Examples 1-3, kits were produced without such colored latex, with gold colloid in amounts relative to OD=1.5 (corresponding to an ordinary concentration for a visual observation kit, and also corresponding to $1.3 \times 10^9$ gold colloid per kit), 0.15, and 0.050 at a wavelength of 520 nm. Moreover, in Comparative Example 4, a kit was produced without gold colloid, and only with a colored latex in an amount relative to OD=0.4 at the absorbance of a wavelength of 850 nm.

(Results)

From the results shown in Table 1, it is found that, when the amount of gold colloid was reduced in order to suppress the generation of false-positive results (line coloration in an antigen concentration of 0 (zero)) after silver amplification, the sensitivity before silver amplification was significantly decreased (Comparative Examples 1, 2 and 3), but that such a decrease in the sensitivity before silver amplification could be improved (Example 1) by the mixing of labeling particles with low silver amplification activity (Comparative Example 4). Moreover, from the results shown in Table 2, it is found that an antigen concentration range capable of line determination could be obtained without waiting the silver amplification reaction, and thus that it became possible to make determination in a shorter time. It is to be noted that the symbol "N.T." indicates that the experiment was not carried out

TABLE 1

| Line determination | | Comparative Example 1 | | Comparative Example 2 | | Comparative Example 3 | | Comparative Example 4 | | Example 1 | |
|---|---|---|---|---|---|---|---|---|---|---|---|
| Gold colloid | | ×1 ($1.3 \times 10^9$ particles/test) OD 1.5 | | ×1/10 ($1.3 \times 10^8$ particles/test) OD 0.15 | | ×1/30 ($4 \times 10^7$ particles/test) OD 0.050 | | Non | | ×1/30 ($4 \times 10^7$ particles/test) OD 0.050 | |
| Colored latex | | Non | | Non | | Non | | ×1 OD 0.4 | | ×1 OD 0.4 | |
| Silver amplification | | Before | After | Before | After | Before | After | Before | After | Before | After |
| Influenza type A antigen concentration | 0 | − | ++ | − | +w | − | − | − | − | − | − |
| | 1/32000 | − | N.T. | − | N.T. | − | − | − | − | − | − |
| | 1/16000 | − | N.T. | − | N.T. | − | +w | − | − | − | +w |
| | 1/4000 | − | N.T. | − | N.T. | − | + | − | − | − | + |
| | 1/800 | +w | N.T. | − | N.T. | − | + | − | − | − | + |
| | 1/400 | + | N.T. | − | N.T. | − | ++ | +w | +w | +w | ++ |

TABLE 1-continued

| Line determination | Comparative Example 1 | | Comparative Example 2 | | Comparative Example 3 | | Comparative Example 4 | | Example 1 | |
|---|---|---|---|---|---|---|---|---|---|---|
| 1/200 | + | N.T. | − | N.T. | − | ++ | + | + | + | ++ |
| 1/20 | ++ | N.T. | +w | N.T. | − | ++ | ++ | ++ | ++ | ++ |
| 1/1 | ++ | N.T. | + | N.T. | − | ++ | ++ | ++ | ++ | ++ |

TABLE 2

| | | Detectable time | | |
|---|---|---|---|---|
| | | Comparative Example 3 | | Example 1 |
| Silver amplification | | Before | After | Before | After |
| Influenza type A antigen concentration | 0 | — | — | — | — |
| | 1/32000 | — | — | — | — |
| | 1/16000 | — | 15 min | — | 15 min |
| | 1/4000 | — | 15 min | — | 15 min |
| | 1/800 | — | 15 min | — | 15 min |
| | 1/400 | — | 15 min | 10 min | 15 min |
| | 1/200 | — | 15 min | ≤5 min | 15 min |
| | 1/20 | — | 15 min | ≤5 min | 15 min |
| | 1/1 | — | 15 min | ≤5 min | 15 min |

Example 2

Detection of hCG (Human Chorionic Gonadotropin) Antigen (Preparation of Labeling Ingredients)

An anti-hCG monoclonal antibody (specificity: Intact-hCG) was allowed to bind to 0.3-μm colored latex (DC02B; manufactured by Bangs Laboratories) and 0.06-μm gold colloid (GC60; manufactured by British BioCell International) used as labeling ingredients. The binding operation was carried out according to ordinary methods.

(Preparation of Labeling Portion 2)

A solution that contained the anti-hCG monoclonal antibody-binding colored latex and the anti-hCG monoclonal antibody-binding gold colloid in any given OD concentrations was applied to a glass fiber pad, and it was then dried, so as to prepare an anti-hCG monoclonal antibody labeling ingredient-coated pad (a labeling portion 2).

(Preparation of Detection Portion 31)

An anti-hCG monoclonal antibody (specificity: β-hCG) was applied in a line shape to a predetermined position of a nitrocellulose membrane (SCHF (registered trademark); Millipore) that was a porous carrier in an amount of 0.5 μl per test, so as to form a detection portion 31. Moreover, an anti-mouse antibody was also applied to the side downstream of the detection portion 31 in an amount of 0.5 μl per test, so as to form a control portion 32 used for confirmation of the reaction. After completion of the aforementioned application, the antibody was naturally dried and was solidified, so as to prepare an anti-hCG monoclonal antibody-solid-phased membrane 3 (a porous carrier, on which the detection portion 31 was disposed).

(Preparation of Detection Device)

A filter used as a dropping portion 5, an anti-hCG monoclonal antibody labeling ingredient-coated pad 2, an anti-hCG monoclonal antibody-solid-phased membrane 3, and a filter used as a liquid absorbing portion 4, were each attached onto an adhesive-added resin, such that the edges of these components were each overlapped by approximately 3 mm, thereby producing an hCG antigen detecting device.

(Reactivity Test)
(Determination Before Amplification)

hCG was dissolved in a PBS buffer that contained 0.1% BSA, so as to prepare hCG solutions having different concentrations to be used for the test. 140 μl of the thus prepared solution was added dropwise to the dropping portion 5. Thereafter, line coloration from labeling ingredients (a gold colloid particle-derived color, a colored latex particle-derived color, or a mixed color thereof), which would appear in the detection portion 31 until 10 minutes after the addition of the antigen solution, was observed by visual observation. Determination was made such that strong coloration was indicated as "++," moderate coloration was indicated as "+," weak coloration was indicated as "+w," and no coloration was indicated as "−." When such line coloration was observed after the addition of the antigen solution, the time at which the coloration strength became "+w" was defined to be a detectable time, and such a detectable time was measured.

(Determination after Amplification)
(Preparation of Silver Amplification Solution)
(Preparation of Amplification Solution A-1)

40 mL of a 1 mol/L iron nitrate aqueous solution produced by dissolving iron (III) nitrate nonahydrate (Wako Pure Chemical Industries, Ltd.; 095-00995) in water, 10.5 g of citric acid (Wako Pure Chemical Industries, Ltd.; 038-06925), 0.1 g of dodecylamine (Wako Pure Chemical Industries, Ltd.; 123-00246), and 0.44 g of a surfactant, $C_9H_{19}$—$C_6H_4$—O—$(CH_2CH_2O)_{50}$H were dissolved in 325 g of water. After all the aforementioned components had been dissolved in the water, 40 mL of nitric acid (10% by weight) was added to the mixed solution, while stirring with a stirrer. Thereafter, 80 mL of the solution was weighed, and 11.76 g of iron (II) ammonium sulfate hexahydrate (Wako Pure Chemical Industries, Ltd.; 091-00855) was added thereto. The obtained mixture was defined as amplification solution A-1.

(Preparation of Amplification Solution A-2)

Water was added to 10 mL of a silver nitrate solution (containing 10 g of silver nitrate), resulting in a total amount of 100 g. This solution was defined as amplification solution A-2 (10% by weight of silver nitrate aqueous solution).

(Preparation of Amplification Solution A)

40 mL of amplification solution A-1 was weighed, and 4.25 mL of amplification solution A-2 was then added thereto, followed by stirring. The obtained mixture was defined as amplification solution A.

(Evaluation)
(Washing)

Ten minutes after the addition of the antigen solution, a washing solution-adding pad 6 (a glass fiber filter cut into a size of 12 mm×10 mm (GF/F manufactured by GE Healthcare)) was pressed against the edge (acting as an upstream edge in the spreading of a washing solution) of the membrane of the immunochromatography kit used for the test, which was determined in the detection portion 31, and a washing solution-absorbing pad 7 (a glass fiber filter cut into a size of 12 mm×15 ram (GF/F manufactured by GE Healthcare)) was pressed against the other edge thereof (acting as a downstream edge), so that the 12-mm edge sides became the washing solution upstream side and downstream side, respectively, on the membrane, and so that each pad was overlapped with the membrane by approximately 2 mm. The angle between the washing solution spreading direction and the test substance spreading direction was set at 90 degrees. 150 μL of the washing solution was spread by capillarity, so that the membrane was washed for 3 minutes.

In the present experiment, the height of a liquid level depending on the shape of a washing solution container during the washing operation, the shape and material of the sample-adding pad of the immunochromatography kit, experimental environment (temperature and humidity), the material and thickness of the absorbent pad, the connection of the absorbent pad with the nitrocellulose membrane, and the like are factors that change the water-absorbing speed and amount of the washing solution. Thus, it is necessary to keep these factors constant in the experiment. The water-absorbing speed and amount of the washing solution absorbed are factors that determine the final washing effects (a decrease in the remaining amount of gold fine particles). This experiment was carried out at an air temperature of 22±3 C.° and a humidity of 50±15%.

(Signal Amplification with Amplification Solution)

After completion of the washing, 100 μL of an amplification solution was added to the membrane, such that the detection zone and control zone thereof were filled with the amplification solution. Thereafter, an amplification reaction was carried out for 1 minute.

After completion of the amplification reaction, the membrane was removed, and it was then fully washed with water for 1 minute. Then, the coloration level of the detection portion 31 was determined by visual observation. Determination was made such that strong coloration was indicated as "++,"

antibody labeling ingredient in an amount relative to OD=0.010 (corresponding to 1/250 amount of an ordinary concentration for a visual observation kit, and also corresponding to $1.0 \times 10^7$ gold colloid per kit) at the absorbance of a wavelength of 520 nm and an anti-hCG monoclonal antibody-binding colored latex in an amount relative to OD=0.7 at the absorbance of a wavelength of 850 nm. In contrast, in Comparative Examples 5-8, kits were produced without such colored latex, with gold colloid in amounts relative to OD=2.5 (corresponding to an ordinary concentration for a visual observation kit, and also corresponding to $2.5 \times 10^9$ gold colloid per kit), 0.25, 0.125, and 0.010 at a wavelength of 520 nm. Moreover, in Comparative Example 9, a kit was produced without gold colloid, and only with a colored latex in an amount relative to OD=0.7 at the absorbance of a wavelength of 850 nm.

(Results)

From the results shown in Table 3, it is found that, when the amount of gold colloid was reduced in order to suppress the generation of false-positive results (line coloration in an antigen concentration of 0 (zero)) after silver amplification, the sensitivity before silver amplification was significantly decreased (Comparative Examples 5, 6, 7 and 8). In addition, a prozone phenomenon occurred in a high concentration of antigen sample (Comparative Example 8). However, a decrease in the sensitivity before silver amplification could be improved and such a prozone phenomenon could also be avoided (Example 2) by the mixing of labeling particles with low silver amplification activity (Comparative Example 9). Moreover, from the results shown in Table 4, it is found that an antigen concentration range capable of line determination could be obtained without waiting the silver amplification reaction, and thus that it became possible to make determination in a shorter time.

TABLE 3

| Line determination | | Comparative Example 5 | | Comparative Example 6 | | Comparative Example 7 | | Comparative Example 8 | | Comparative Example 9 | | Example 2 | |
|---|---|---|---|---|---|---|---|---|---|---|---|---|---|
| Gold colloid | | ×1 ($2.5 \times 10^9$ particles/test) OD 2.5 | | ×10 ($2.5 \times 10^8$ particles/test) OD 0.25 | | ×1/20 ($1.3 \times 10^8$ particles/test) OD 0.125 | | ×1/250 ($1.0 \times 10^7$ particles/test) OD 0.010 | | Non | | ×1/250 ($1.0 \times 10^7$ particles/test) OD 0.010 | |
| Colored latex | | Non | | Non | | Non | | Non | | ×1 OD 0.7 | | ×1 OD 0.7 | |
| Silver amplification | | Before | After | Before | After | Before | After | Before | After | Before | After | Before | After |
| hCG antigen concentration (mIU/mL) | 0 | − | ++ | − | + | − | +w | − | − | − | − | − | − |
| | 0.5 | − | N.T. | − | N.T. | − | N.T. | − | − | − | − | − | − |
| | 1 | − | N.T. | − | N.T. | − | N.T. | − | +w | − | − | − | +w |
| | 10 | − | N.T. | − | N.T. | − | N.T. | − | + | − | − | − | + |
| | 50 | + | N.T. | − | N.T. | − | N.T. | − | + | +w | +w | +w | + |
| | 100 | + | N.T. | +w | N.T. | − | N.T. | − | ++ | + | + | + | ++ |
| | 1,000 | ++ | N.T. | + | N.T. | +w | N.T. | − | ++ | ++ | ++ | ++ | ++ |
| | 10,000 | ++ | N.T. | ++ | N.T. | + | N.T. | − | ++ | ++ | ++ | ++ | ++ |
| | 100,000 | ++ | N.T. | +w | N.T. | − | N.T. | − | ++ | ++ | ++ | ++ | ++ |
| | 1,000,000 | + | N.T. | − | N.T. | − | N.T. | − | +w | + | + | + | + |
| | 2,000,000 | + | N.T. | − | N.T. | − | N.T. | − | − | + | + | + | + | moderate coloration was indicated as "+," weak coloration was indicated as "+w," and no coloration was indicated as "−."

Example 2

Comparative Examples 5-9

Kits, in which the amounts of colored latex and gold colloid were varied, were produced by the above-described production method, and were then evaluated (Table 3). In Example 2, a kit was produced using an anti-hCG monoclonal

TABLE 4

| | | Detectable time | | | |
|---|---|---|---|---|---|
| | | Comparative Example 7 | | Example 2 | |
| Silver amplification | | Before | After | Before | After |
| hCG antigen concentration | 0 | — | — | — | — |
| | 0.5 | — | — | — | — |

TABLE 4-continued

| | | Detectable time | | | |
|---|---|---|---|---|---|
| | | Comparative Example 7 | | Example 2 | |
| Silver amplification | | Before | After | Before | After |
| (mIU/mL) | 1 | — | 15 min | — | 15 min |
| | 10 | — | 15 min | — | 15 min |
| | 50 | — | 15 min | 10 min | 15 min |
| | 100 | — | 15 min | 5 min | 15 min |
| | 1,000 | — | 15 min | ≤5 min | 15 min |
| | 10,000 | — | 15 min | ≤5 min | 15 min |
| | 100,000 | — | 15 min | ≤5 min | 15 min |
| | 1,000,000 | — | 15 min | ≤5 min | 15 min |
| | 2,000,000 | — | — | ≤5 min | 15 min |

The invention claimed is:

1. An immunochromatography method, which comprises:

spreading a test substance, a first labeling substance modified with a first binding substance that binds to the test substance, and a second labeling substance modified with the first binding substance that binds to the test substance, which are in a mixed state, on an insoluble carrier;

capturing the test substance, the first labeling substance, and/or the second labeling substance at a reaction site on the insoluble carrier comprising an immobilizing reagent capable of binding to the test substance, so as to detect the test substance, measuring the second labeling substance at the reaction site on the insoluble carrier; and thereafter amplifying the first labeling substance at the reaction site on the insoluble carrier; and thereafter measuring the first labeling substance at the reaction site on the insoluble carrier, wherein the first labeling substance is a labeling substance that causes an amplification reaction, and the second labeling substance is a labeling substance that does not substantially influence on the amplification reaction, wherein the first labeling substance is a metal colloid and the second labeling substance is a colored particle, and wherein the first labeling substance is a substance that reacts with silver ions and a reducing agent used for such silver ions to generate metallic silver, and the second labeling substance is a substance that does not substantially have a reactivity with silver ions and a reducing agent used for the silver ions, and wherein the number of metal colloid particles which are applied to the insoluble carrier is from $1 \times 10^5$ or more to $1 \times 10^8$ or less.

2. The immunochromatography method according to claim 1, wherein the metallic silver is generated as a result of an amplification reaction using silver ions and a reducing agent used for the silver ions.

3. The immunochromatography method according to claim 1, wherein the metal colloid includes gold, silver or platinum.

* * * * *